United States Patent [19]

Sundt et al.

[11] 4,251,398
[45] Feb. 17, 1981

[54] CYCLOHEXYL-PENTANOLIDES AND THEIR USE IN PERFUME

[75] Inventors: Erling Sundt, Vessy, Ge; Roland Aschiero, Bernex, Ge; Walter Schenk, Geneva, all of Switzerland

[73] Assignee: Firmenich SA, Geneva, Switzerland

[21] Appl. No.: 87,510

[22] Filed: Oct. 23, 1979

Related U.S. Application Data

[62] Division of Ser. No. 2,178, Jan. 9, 1979, abandoned.

[51] Int. Cl.³ .................................................. C11B 9/00
[52] U.S. Cl. .......................... 252/522 R; 260/343.5;
252/174.17; 424/69; 424/358; 424/76
[58] Field of Search .................. 252/52.2; 260/343.5

[56] References Cited

PUBLICATIONS

J. Bryan Jones et al., J. Org. Chem. 42, No. 19, 3206–3208, 1977 Chem. Ab. 87: 134925 K, 1977.
Jean Pierre Fourneau, Ind. Parfum 3, 109–119, 1948. Chem. Ab. 45: 1161 e, 1951.

*Primary Examiner*—Veronica O'Keefe

[57] ABSTRACT

New lactones having the formula

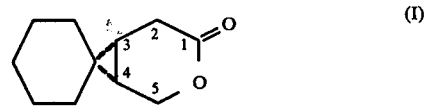

wherein the cyclohexyl radical is bound to the carbon atoms at position 3 or 4 as indicated by the dotted lines, their use as perfuming ingredients and process for their preparation.

3 Claims, No Drawings

CYCLOHEXYL-PENTANOLIDES AND THEIR USE IN PERFUME

This is a division of application Ser. No. 2,178, filed Jan. 9, 1979, now abandoned.

SUMMARY OF THE INVENTION

The present invention relates to novel lactones having the formula

wherein the cyclohexyl radical is bound to the carbon atoms at position 3 or 4 of the lactonic ring as indicated by the dotted lines, viz, 3-cyclohexyl-pentanolide and 4-cyclohexyl-pentanolide.

The invention also relates to a perfume, a perfume composition or a perfumed article, which comprises as an olfactively active ingredient a compound of formula (I) as set forth hereinabove, as well as to a method for modifying, improving or enhancing the olfactive properties of perfumes, perfume compositions or perfumed articles, which comprises adding thereto an olfactively effective amount of said compound of formula (I).

The invention further relates to a process for preparing a compound of formula (I) as set forth hereinabove, which comprises
(A) treating cinnamic aldehyde with ethyl vinyl ether to afford 2-ethoxy-4-phenyl-3,4-dihydro-2H-pyran, hydrogenating the resulting product to afford 3-cyclohexylpentane-1,5-diol and finally heating the above diol in the presence of a dehydrogenation catalyst to afford 3-cyclohexyl-pentanolide; or
(B) treating 3-cyclohexyl-cyclopentanone with an organic peracid to afford a mixture of 3-cyclohexyl-pentanolide and 4-cyclohexyl-pentanolide.

BACKGROUND OF THE INVENTION

In a constant undertaking towards the replacement of costly natural materials or the reproduction of original fragrance notes, the perfume industry devotes a treat deal of efforts to synthesize new odoriferous compounds starting from easily available raw materials.

Several alkyl-substituted lactones, more specifically those lactones substituted with a linear alkyl radical, have been proposed in the past as perfuming ingredients. As an example, one can cite delta-undecalactone which is characterized by its powerful fatty, creamy and peach-like odour of excellent tenacity—see S. Arctander, Perfumes and Flavor Chemicals, Montclair N.J. 1969; Section 3025—, as well as delta-decalactone and delta-dodecalactone which are both appreciated in the field of perfumery for their strong and tenacious odour of fruity, nutty, oily and creamy type—see S. Arctander, op. cit.; Sections 829 and 1103, respectively.

We have surprisingly found that, contrary to the teaching of the art, the compounds of formula (I), viz, 3-cyclohexyl-pentanolide and 4-cyclohexyl-pentanolide, basically differ from the above prior known lactones in respect of their odouriferous properties and that they could be advantageously used in the field of perfumery, as ingredients for the preparation of perfume compositions for example.

PREFERRED EMBODIMENTS OF THE INVENTION

The compounds of formula (I) are characterized by their original, particularly powerful and tenacious odour, at the same time sweet and spicy, reminiscent of certain aspects of coumarin. By the use of compounds of formula (I), the perfumer is now able to reproduce new and original olfactive nuances in the field of the spicy odour notes. Due to their tenacity the compounds of formula (I) are also appreciated for the enhancement of the "ground" notes of lavender, spicy or coumarin type perfume compositions.

In fact, the compounds of formula (I) may find a wide range of applications, for example for modifying or enhancing various odouriferous notes such as flowery, fruity, woody, spicy, chypre or "Fougère" notes. They can also be advantageously used for perfuming a variety of articles such as soaps, detergents, household materials or cosmetic preparations for example.

In order to achieve the desired effects, the compounds of formula (I) can be used in proportions comprised in a very wide range of values. These values depend on the nature of the added coingredients as well as on that of the materials to which they are added and on the effects it is desired to achieve. For the preparation of perfume compositions for instance, they can be used in proportions comprised between about 0.1 and 10 or even 20% by weight based on the total weight of the finished composition, the most interesting effects being obtained by the use of proportions comprised between about 1 and 10%. These quantities, however, are given in a purely examplificatory manner.

According to the process of the present invention, both compounds of formula (I), viz, 3-cyclohexyl-pentanolide and 4-cyclohexyl-pentanolide, can be easily prepared from 3-cyclohexyl-cyclopentanone by the treatment of the latter with an organic peracid. Said treatment, which proceeds in accordance with the Bayer-Villiger type reaction, may be effected according to the known techniques [see for example H. O. House, Modern Synthetic Reactions, W. A. Benjamin, Inc., New York (1965), p. 123 and ff.]. Thus, for example, the mentioned reaction can suitably be performed by the action of a peracid such as performic, peracetic, trifluoro-peracetic, monopermaleic, perbenzoic or monoperphthalic acid; performic and peracetic acid are preferred. The organic peracid can also be generated in situ by the action of hydrogen peroxide on the corresponding organic acid. The reaction can be effected in an aqueous medium in the presence of an inert organic solvent such as a halogenated hydrocarbon, e.g. dichloromethane, dichloroethane, chloroforme, trichloroethylene or dichloroethylene. The reaction can also be effected in a buffered medium, for example in the presence of alkali metal salts of organic carboxylic acids. To this purpose, sodium or potassium formate, acetate, propionate, butyrate, oxalate, citrate or tartrate can be conveniently used.

As directly prepared by the above process, the obtained reaction product consists in a mixture of 3-cyclohexyl-pentanolide and 4-cyclohexyl-pentanolide, which products can be used as such in accordance with the present invention; we noted in fact that a separation of the above mixture into its two constituents is not necessary for achieving the desired odouriferous effects.

Whenever such a separation is requested however, both 3-cyclohexyl-pentanolide and 4-cyclohexyl-pentanolide may be isolated in their pure state through the formation of the mixture of the corresponding unsaturated derivatives, viz, 3-cyclohexyl-pent-2-ene-olide and 4-cyclohexyl-pent-2-ene-olide respectively [according to the method described by Sharpless et al. in J. Amer. Chem. Soc., 95, 6137 (1977)], separation of the above two unsaturated lactones and subsequent hydrogenation—for the details of such a separation see Example 2.

3-Cyclohexyl-cyclopentanone used hereinabove as starting material can be obtained for instance by treating cyclopent-2-ene-1-one with cyclohexyl chloride, in the presence of cuprous salts as described in Example 2 of the present specification.

According to another embodiment of the process of the present invention, pure 3-cyclohexyl-pentanolide can be easily prepared starting from cinnamic aldehyde and ethyl vinyl ether, hydrogenation of the resulting product and subsequent heating of the said hydrogenation product in the presence of a dehydrogenation catalyst.

The first step of the above process consists in a Diels-Alder cyclo-addition of ethyl vinyl ether to cinnamic aldehyde and is effected as described in J. Amer. Chem. Soc., 72, 3079 (1950).

The thus obtained 2-ethoxy-4-phenyl-3,4-dihydro-2H-pyran is then subjected to hydrogenation to afford 3-cyclohexyl-pentane-1,5-diol. Such a hydrogenation is carried out according to the techniques used in the art for reducing aromatic compounds into the corresponding cyclohexyl derivatives, namely at high pressure and in the presence of a metal catalyst. Catalysts such as platinum oxide, Raney nickel, rhodium or ruthenium for example may be conveniently used to this effect, the hydrogenation being carried out at a pressure of the order of about 50 to 300 atmospheres, preferably in a stainless steel autoclave. According to a preferred embodiment of the process of present invention, the said hydrogenation is effected in the presence of ruthenium on charcoal, at a pressure of about 200 atmospheres.

The subsequent treatment of the 3-cyclohexylpentane-1,5-diol thus obtained consists in heating this latter in the presence of a dehydrogenation catalyst. This interconversion of the above diol into the corresponding lactone can be effected in the presence of the dehydrogenation catalysts commonly used in the art [see e.g. Houben-Weyl, Methoden der organischen Chemie, VI/2, p. 717 and ff. (1963)]. Metal catalysts such as copper, copper chromite, silver, nickel or cobalt e.g., may be conveniently used, at temperatures of from about 220° to 320° C. According to a preferred embodiment of the present process, the said reaction is effected in the presence of a copper containing catalyst, at a temperature of the order of about 260° C.

The present invention will be better illustrated by the following examples wherein the temperatures are given in degrees centigrade and the abbreviations have the sense common in the art.

EXAMPLE 1

3-Cyclohexyl-pentanolide (a) 313 g (2.37 Mole) of cinnamic aldehyde, 290 g (4.03 Mole) of ethyl vinyl ether and 45 g of hydroquinone were heated at 200° for 16 hours in a 1 l stainless steel autoclave (pressure about 20 atm.). After fractional distillation of the crude material thus obtained, there were isolated 422 g (87% yield) of 2-ethoxy-4-phenyl-3,4-dihydro-2H-pyran, b.p. 89°/0.02 Torr;

IR: 1640, 1230, 1095, 1030, 700 cm$^{-1}$; NMR(90 MHz): signals at 1.27, 2.02, 3.82, 4.8, 5.08, 6.81 and 7.28 $\delta$ ppm, MS: 204 (9), 175 (1), 158 (90), 145 (2), 131 (86), 115 (23), 104 (29), 91 (25), 72 (100), 63 (3), 51 (15), 43 (84).

(b) 150 g (0.735 Mole) of the above compound, 26.5 g of water (1.47 Mole) and 150 g of 1,2-dimethoxy-ethane were hydrogenated in a stainless steel autoclave in the presence of 3.0 g of ruthenium 5% on charcoal for 20 hours (temperature 165°; pressure 200 atm. H$_2$). After cooling to room temperature, filtration and evaporation under reduced pressure there were obtained 172 g of raw material. Fractional distillation thereof finally gave 100 g (73% yield) of 3-cyclohexyl-pentane-1,5-diol, b.p. 137°/0.01 Torr.

IR: 3330, 1740, 1460, 1060, 920 cm$^{-1}$; NMR(60 MHz): signals at 1.2, 1.52, 2.25 and 3.68 $\delta$ ppm; MS: m/e: 150 (2), 140 (27), 124 (26), 109 (16), 96 (44), 83 (53), 68 (68), 67 (68), 55 (100), 41 (65).

(c) 800 g of copper oxide at 50% on a mineral carrier were poured into a glass column (length: 90 cm; $\phi$ 3 cm), hydrogenated according to conventional techniques and the thus prepared column was fixed to a 250 ml reaction vessel. The whole apparatus was kept under reduced pressure (1 Torr), the vessel being heated at 300° and the column at 260°. 115 g (0.61 Mole) of 3-cyclohexyl-pentane-1,5-diol were then introduced dropwise into the hot vessel (rate 15 g/hour) and evaporated through the column to give 104 g of a raw material consisting of about 75% 3-cyclohexyl-pentanolide and 25% 3-cyclohexyl-3,4-dihydro-2H-pyran. Fractional distillation of the above material finally gave 70 g (62% yield) of the desired product in its pure state, b.p. 116°/0.2 Torr.

IR: 1740, 1445, 1400, 1250, 1230, 1170, 1080 cm$^{-1}$ NMR(90 MHz): signals at 1.2, 1.75, 2.23, 2.68 and 4.22 $\delta$ ppm; MS: m/e: 137 (1), 109 (3), 100 (86), 99 (100), 83 (28), 67 (23), 55 (69), 41 (46).

EXAMPLE 2

3-Cyclohexyl-pentanolide and 4-cyclohexyl-pentanolide 138.0 g (3 Mole) of 98% formic acid and 8.9 g (0.25 Mole) of hydrogen peroxide 35% in water were poured into a 500 ml vessel, under nitrogen atmosphere. To the above mixture, heated at 40°, 33.2 g (0.20 Mole) of 3-cyclohexyl-cyclopentanone were progressively added (ca. 1 hour; reaction temperature: 40°–50°). The reaction mixture was further stirred for 1 hour and the excess of formic acid taken off under reduced pressure. The thus obtained residue was then extracted with methylene chloride (3×100 ml), washed with a saturated NaHCO$_3$ aqueous solution (3×30 ml), then with water (2×50 ml), dried over sodium sulfate and finally evaporated to afford, after distillation on a VIGREUX column, 29.2 g (80% yield) of a 65:35 mixture of 3-cyclohexyl-pentanolide and 4-cyclohexyl-pentanolide, b.p. 110°–115°/0.01 Torr.

The thus obtained mixture, which could be used as such according to the present invention, was characterized as indicated hereinafter.

IR: 1740, 1450, 1405, 1258, 1185, 1080 cm$^{-1}$; NMR(90 MHz): signals at 1.14; 1.74, 2.41 and 4.24 $\delta$ ppm, MS: m/e: 164 (5), 151 (4), 134 (7), 127 (9), 109 (8), 100 (93), 99(100), 81 (35), 67 (37), 55 (81), 41 (51).

The determination of the relative proportions of 3-cyclohexyl-pentanolide and 4-cyclohexyl-pentanolide in the above mixture, as well as their preparation in pure state, was effected as follows: 3.0 g of the above mixture was treated with phenyl-selenium chloride according to the method described by Sharpless et al. in J. Amer. Chem. Soc., 95, 6137 (1973) to afford, after distillation on a VIGREUX column (b.p. 107°/0.01 Torr), 1.5 g of a product consisting of about 20% of unreacted starting material and about 80% of a 65:35 mixture of 3-cyclohexylpent-2-ene-olide and 4-cyclohexyl-pent-2-ene-olide, according to the vapour phase chromatography analysis (APIEZON L on CHROMOSORB 60–80 Mesh—215°—120 ml He/min—2.5 m length).

Each of the above mentioned pent-2-ene-olides was then isolated separately, by means of the above vapour phase chromatography and finally hydrogenated at atmospheric pressure (solvent: ethyl alcohol—catalyst: palladium 5% on charcoal) to give (a) 3-cyclohexyl-pentanolide (identification: see Example 1) and (b) 4-cyclohexyl-pentanolide IR: 1740, 1445, 1400, 1235, 1180, 1050 cm$^{-1}$, NMR(90 MHz): signals at 1.22, 1.82, 2.54, 3.91 and 4.51 δ ppm. MS: m/e: 182 (9), 164 (21), 151 (20), 134 (31), 127 (37), 109 (27), 100 (48), 81 (71), 67 (70), 55 (100), 41 (77).

3-Cyclohexyl-cyclopentanone used hereinabove as starting material was prepared as indicated hereinafter: 16.6 g (0.148 Mole) of cyclohexyl chloride were added dropwise to 3.6 g (0.150 atome-g) of magnesium metal in a 250 ml vessel, under nitrogen atmosphere and in the presence of a iodine cristal. The reaction mixture was heated to reflux for 1 hour, then cooled to 0° and 1.42 g (0.074 Mole) of cuprous iodide were added thereto. After cooling the reaction mixture at −8°, 5.74 g (0.070 Mole) of cyclopent-2-ene-1-one in 40 ml of tetrahydrofurane were added dropwise. After having been stirred for 1 hour at −8°, the reaction mixture was poured onto 100 g of crushed ice, acidified with 15% HCl in water (pH 4–5) and finally neutralized by the addition of aqueous ammonia. After the addition of 10 g of NH$_4$Cl the reaction mixture was extracted with ether (3×300 ml), washed with water (3×100 ml), dried over sodium sulfate and finally evaporated to afford 13.2 g of raw material. After purification by means of column chromatography (neutral Al$_2$O$_3$—eluent:toluene) and subsequent distillation on a VIGREUX column, there were obtained 7.0 g (60% yield) of the desired product, b.p. 50°/0.005 Torr.

IR: 1745, 1450, 1400, 1160 cm$^{-1}$, NMR(60 MHz): signals at 1.1, 1.73, 2.15 and 2.49 δ ppm MS: m/e: 166 (30), 137 (15), 122 (11), 109 (5), 84 (52), 83 (100), 67 (24), 55 (69), 41 (34).

EXAMPLE 3

A base perfume composition of "Fougère" type was prepared by admixing the following ingredients (parts by weight):

| Musc xylene | 30 |
| Heliotropin | 50 |
| Benzyl salicylate | 30 |
| Amyl salicylate | 50 |
| Methyl dihydrojasmonate[1] | 20 |
| Cyclamen aldehyde | 20 |
| Patchouli oil | 20 |
| Phenylethyl alcohol | 70 |
| Linalool | 100 |
| Geraniol | 100 |
| Benzyl acetate | 50 |
| Terpenyl acetate | 100 |
| Petitgrain oil | 40 |
| Synthetic geranium oil | 100 |
| Synthetic bergamot oil | 120 |
| Lavandin oil | 100 |
| Total | 1000 |

[1]HEDIONE® (FIRMENICH, SA)

The above base, which may be defined as a classical "Fougère" composition, is advantageously used for the preparation of perfumed products such as lotions, toilet soaps or beauty creams for example.

The above base was then used for preparing the following perfume compositions (parts by weight):

| Ingredients | Comp. A | Comp. B | Comp. C |
| --- | --- | --- | --- |
| Base composition | 900 | 900 | 950 |
| 3-Cyclohexyl-pentanolide | 100 | — | — |
| Product of Example 2[1] | — | 100 | — |
| Coumarin | — | — | 50 |
| Total | 1000 | 1000 | 1000 |

[1]65:35 mixture of 3-cyclohexyl-pentanolide and 4-cyclohexyl-pentanolide.

The thus prepared perfume compositions were finally subjected to an olfactive evaluation by a group of perfume experts and characterized as follows:

Composition A: Possesses a more powerful and tenacious odour than that of the base. Well marked lavender note.

Composition B: Stronger and more tenacious than the base. Well marked lavender note.

Composition C: Stronger and more tenacious odour than that of the base. Lavender note more pronounced than that of compositions A and B.

EXAMPLE 4

The following toilet soaps were prepared by mixing the ingredients mentioned hereinafter according to the usual techniques (parts by weight):

| Ingredients | Soap A | Soap B |
| --- | --- | --- |
| Commercial soap paste | 1000 | 1000 |
| 3-Cyclohexyl-pentanolide | 5 | — |
| Product of Example 2[1] | — | 5 |

[1]65:35 mixture of 3-cyclohexyl-pentanolide and 4-cyclohexyl-pentanolide.

The thus prepared toilet soaps were then subjected to an olfactive evaluation and characterized as follows:

Soap A: Possesses a pleasant fresh and spicy odour; reminiscent of certain aspects of lavender Soap B: Pleasant fresh and spicy odour; reminiscent of certain aspects of lavender.

EXAMPLE 5

A perfumed detergent powder was prepared by mixing the following ingredients according to the usual techniques (parts by weight):

| Ingredients | Sample A | Sample B |
| --- | --- | --- |
| Commercial detergent powder | 1000 | 1000 |
| 3-Cyclohexyl-pentanolide | 2 | — |
| Product of Example 2[1] | — | 2 |

[1]65:35 mixture of 3-cyclohexyl-pentanolide and 4-cyclohexyl-pentanolide.

The thus prepared two samples were then subjected to an olfactive evaluation and characterized as follows.

Sample A: Possesses a pleasant fresh and spicy odour; reminiscent of certain aspects of lavender Sample B: Pleasant fresh and spicy odour; reminiscent of certain aspects of lavender.

What we claim is:

1. A lactone having the formula

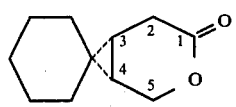
(I)

wherein the cyclohexyl radical is bound to the carbon atoms at position 3 or 4 of the lactonic ring as indicated by the dotted lines.

2. A perfume or perfume composition which comprises as an olfactively active ingredient, a compound having the formula

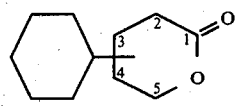

wherein the cyclohexyl radical is bound to the carbon atoms at position 3 or 4 of the lactonic ring in an amount sufficient to modify or enhance the flowery, fruity, woody, spicy, chypre or "Fougery" notes in said perfume or perfume composition.

3. Method for modifying, improving or enhancing the olfactive properties of perfumes or perfume compositions, which comprises adding thereto a compound having the formula

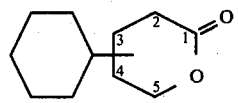

wherein the cyclohexyl radical is bound to the carbon atoms at positions 3 or 4 or the lactonic ring in an amount sufficient to modify or enhance the flowery, fruity, woody, spicy, chypre or "Fougery" notes in said perfume or perfume composition.

* * * * *

UNITED STATES PATENT AND TRADEMARK OFFICE
CERTIFICATE OF CORRECTION

PATENT NO. : 4,251,398

DATED : February 17, 1981

INVENTOR(S) : Erling Sundt, et al

It is certified that error appears in the above—identified patent and that said Letters Patent is hereby corrected as shown below:

Column 1, line 46, "a treat deal" should read

-- a great deal --.

Signed and Sealed this

Twenty-third Day of June 1981

[SEAL]

Attest:

RENE D. TEGTMEYER

Attesting Officer

Acting Commissioner of Patents and Trademarks

Disclaimer

4,251,398.—*Erling Sundt;* Vessy/Ge, *Roland Aschiero;* Bernex, Ge, and *Walter Schenk;* Geneva, Switzerland. CYCLOHEXYLPENTANOLIDES AND THEIR USE IN PERFUME. Patent dated Feb. 17, 1981. Disclaimer filed May 11, 1981, by the assignee, *Firmenich SA.*

Hereby enters this disclaimer to claim 1 of said patent.

[*Official Gazette August 18, 1981.*]

Disclaimer 4,251,398.—*Erling Sundt*, Vessy/Ge, *Roland Aschiero*, Bernex/Ge and *Walter Schenk*, Geneve, Switzerland. CYCLOHEXYL-PENTANOLIDES AND THEIR USE IN PERFUME. Patent dated Feb. 17, 1981. Disclaimer filed May 11, 1981, by the assignee, *Firmenich SA*.

Hereby enters this disclaimer to claim 1 of said patent.

[*Official Gazette December 29, 1981.*]

UNITED STATES PATENT AND TRADEMARK OFFICE
CERTIFICATE OF CORRECTION

PATENT NO. : 4,251,398

DATED : February 17, 1981

INVENTOR(S) : Erling Sundt, et al.

It is certified that error appears in the above—identified patent and that said Letters Patent is hereby corrected as shown below:

On the title page Insert

-- (30) Foreign Application Priority Data
    January 20, 1978    Switzerland    620/78 --

Signed and Sealed this

Thirteenth Day of April 1982

[SEAL]

Attest:

Attesting Officer

GERALD J. MOSSINGHOFF

Commissioner of Patents and Trademarks